United States Patent [19]

Abbott

[11] Patent Number: 5,191,783
[45] Date of Patent: Mar. 9, 1993

[54] PORTABLE BASKETBALL RIM TESTING DEVICE

[76] Inventor: W. Bruce Abbott, 610 Clover St., Cheney, Wash. 99004

[21] Appl. No.: 691,386

[22] Filed: Apr. 25, 1991

[51] Int. Cl.[5] .......................... G01L 1/04; G01N 3/08
[52] U.S. Cl. .......................... 73/12.06; 73/862.642; 73/12.01
[58] Field of Search .................. 73/12, 11, 862.62, 79; 273/1.5 R, 1.5 A

[56] References Cited

U.S. PATENT DOCUMENTS

| | | | |
|---|---|---|---|
| 2,587,628 | 3/1952 | King | 73/11 |
| 2,619,956 | 12/1952 | Torricelli | 128/2 |
| 2,740,287 | 4/1956 | Gindraux | 73/12 |
| 2,854,847 | 10/1958 | Brady | 73/100 |
| 2,888,821 | 6/1959 | Duffy et al. | 73/4 |
| 2,923,147 | 2/1960 | MacMillan | 73/11 |
| 2,972,329 | 2/1961 | Smith | 116/114 |
| 3,214,966 | 11/1965 | Menzies | 73/79 |
| 3,349,620 | 10/1967 | Speiser | 73/379 |
| 3,552,184 | 1/1971 | Breese et al. | 73/12 |
| 3,811,316 | 5/1974 | Amendolia | 73/11 |
| 3,859,841 | 1/1975 | Evans et al. | 73/12 |
| 3,879,982 | 4/1975 | Schmidt | 73/12 |
| 3,981,174 | 9/1976 | Himmler | 73/11 |
| 4,006,626 | 2/1977 | Ruzicka et al. | 73/13 |
| 4,023,396 | 5/1977 | Yakshin et al. | 73/12 |
| 4,034,603 | 7/1977 | Leeb et al. | 73/79 |
| 4,426,875 | 1/1984 | Crosby | 73/12 |
| 4,495,792 | 1/1985 | Bai et al. | 73/12 |
| 4,761,991 | 8/1988 | Fembock | 73/11 |
| 4,799,375 | 1/1989 | Lally | 73/12 |
| 4,880,239 | 11/1989 | Leneveu | 273/181 F |

OTHER PUBLICATIONS

"National Association of Basketball Coaches Research Committee" Report re: Rim Elasticity Tests-Basketball Products International Device, No. F/88-89/JVK.
"National Association of Basketball Coaches Research Committee" report re: Rim Elasticity Test-Ronan and Kunzl Device, No. SU/88/JVK.
Krause, Jerry, et al., "The Effects of a Target Rim on Basketball Shooting Accuracy", Research Study, Lexington, KY., NABC Research Committee (1985 NABC Convention).
Krause, Jerry, et al., "An Equipment Research Project of Rims/Backboards/Support Systems", Lexington, KY., NABC Annual Convention (Mar. 1985).
Krause, Jerry, "Rebound Tests on Various Basketball Rims" for NCAA, Report No. 2099 (Jun. 3, 1986).

*Primary Examiner*—Donald O. Woodiel
*Attorney, Agent, or Firm*—Wells, St. John, Roberts, Gregory & Matkin

[57] ABSTRACT

A portable basketball rim rebound testing device 10 is illustrated as a preferred embodiment for testing the rebound characteristics of a basketball rim 12 and its accompanying support system to determine the rebound characteristics of the system. The apparatus 10 includes a depending frame 28 having a "C" shaped hook 36 for releasably rigidly connecting the frame to the basketball rim 12. A free weight 60 is mounted on a guide rod 52 permitting the free weight to be dropped and impacting against face plate 56 and ceramic washer 58 to generate a sharp force impulse for deflecting the basketball rim downwardly and then permitting the rim to vibrate. A transducer 24 is mounted on the depending frame 28 to sense either the acceleration or the force being applied to the basketball rim 12 for a period of approximately 50 milliseconds to obtain sufficient information to calculate the rebound characteristics. In this embodiment, a signal processing means 26 to the transducer to process the electrical signal and to determine the magnitude of the force, the average force and to integrate the force over time to determine the impulse applied and absorbed by the basketball rim to determine the rebound characteristics of the basketball rim in a very accurate and consistent manner.

35 Claims, 4 Drawing Sheets

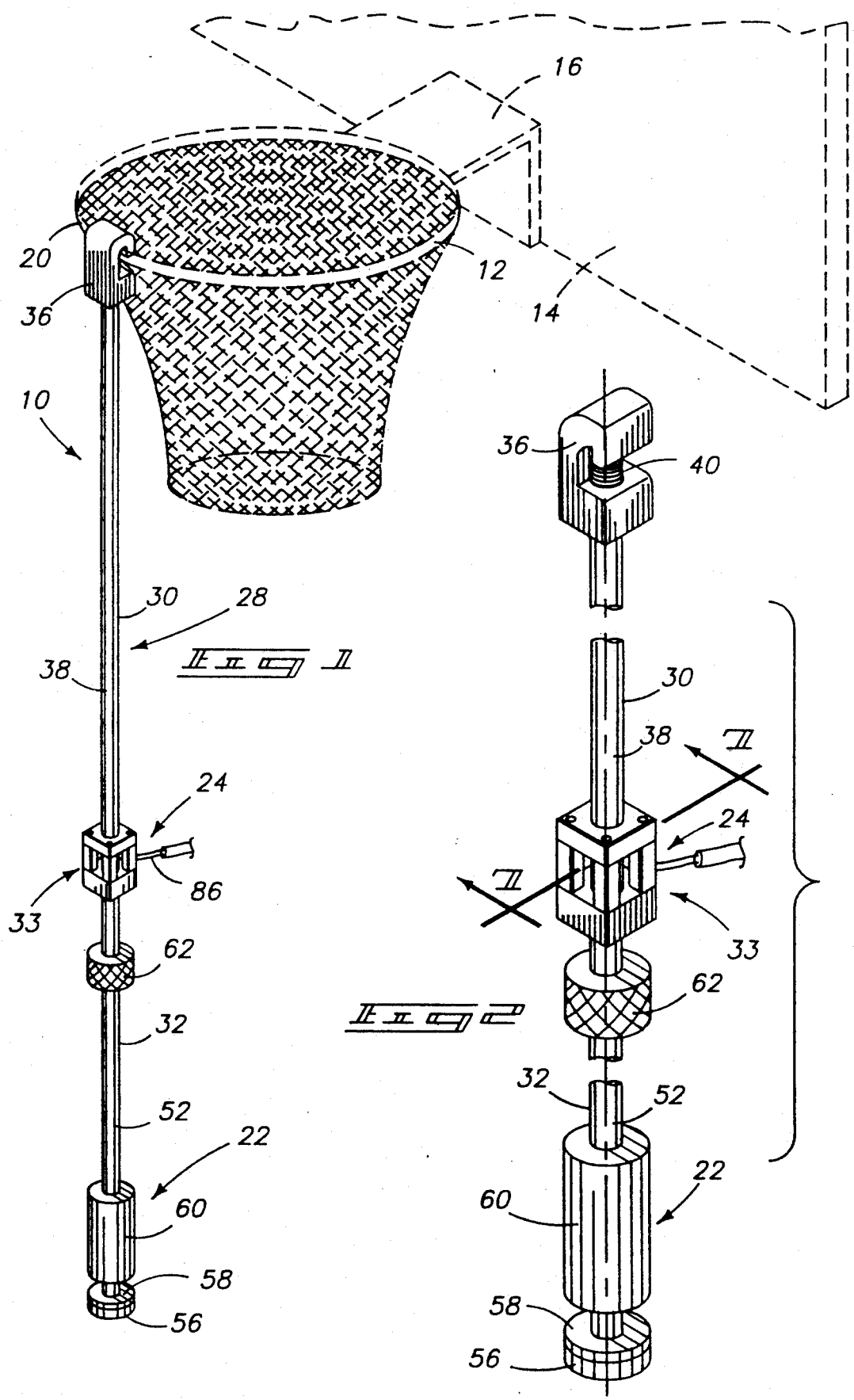

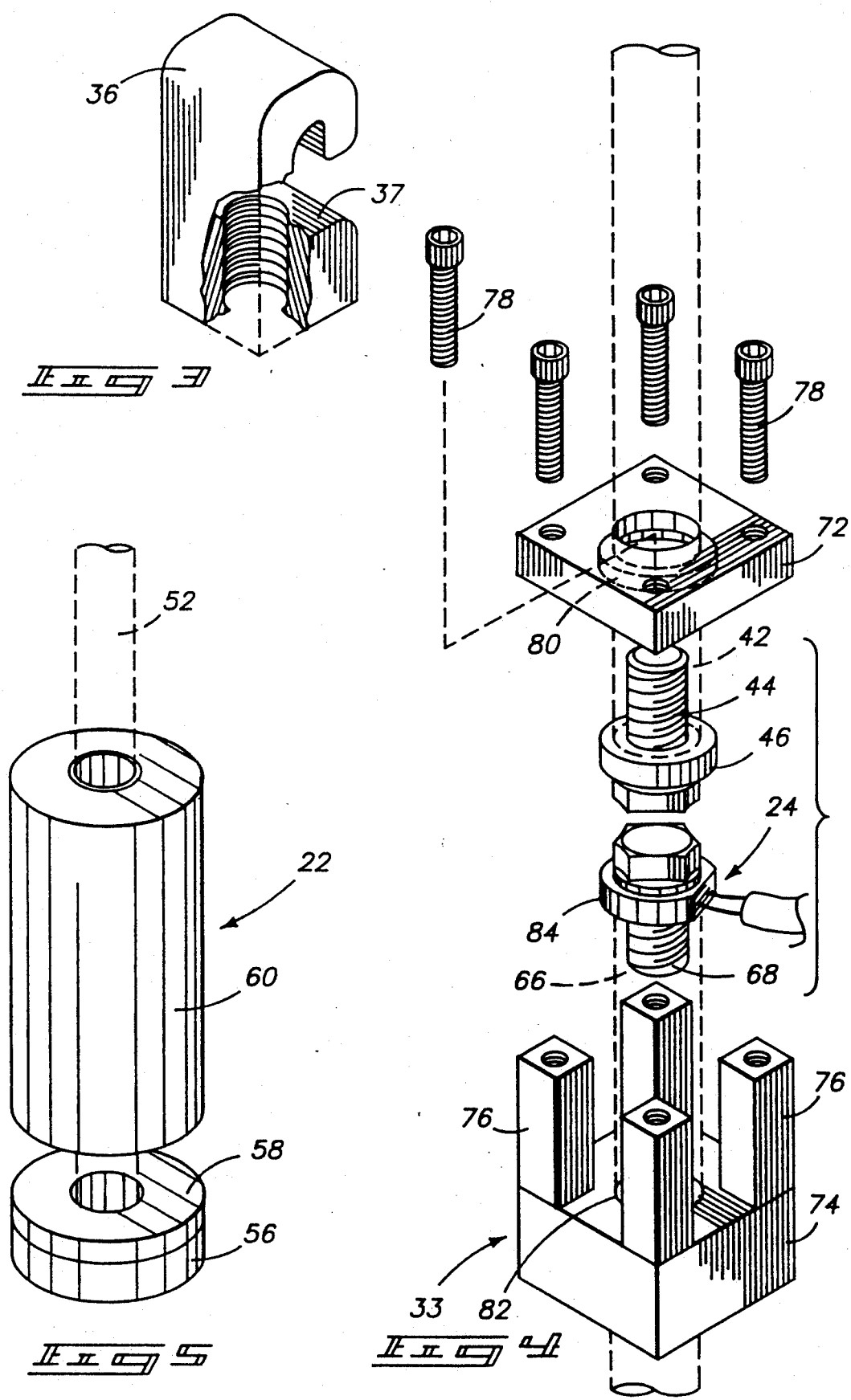

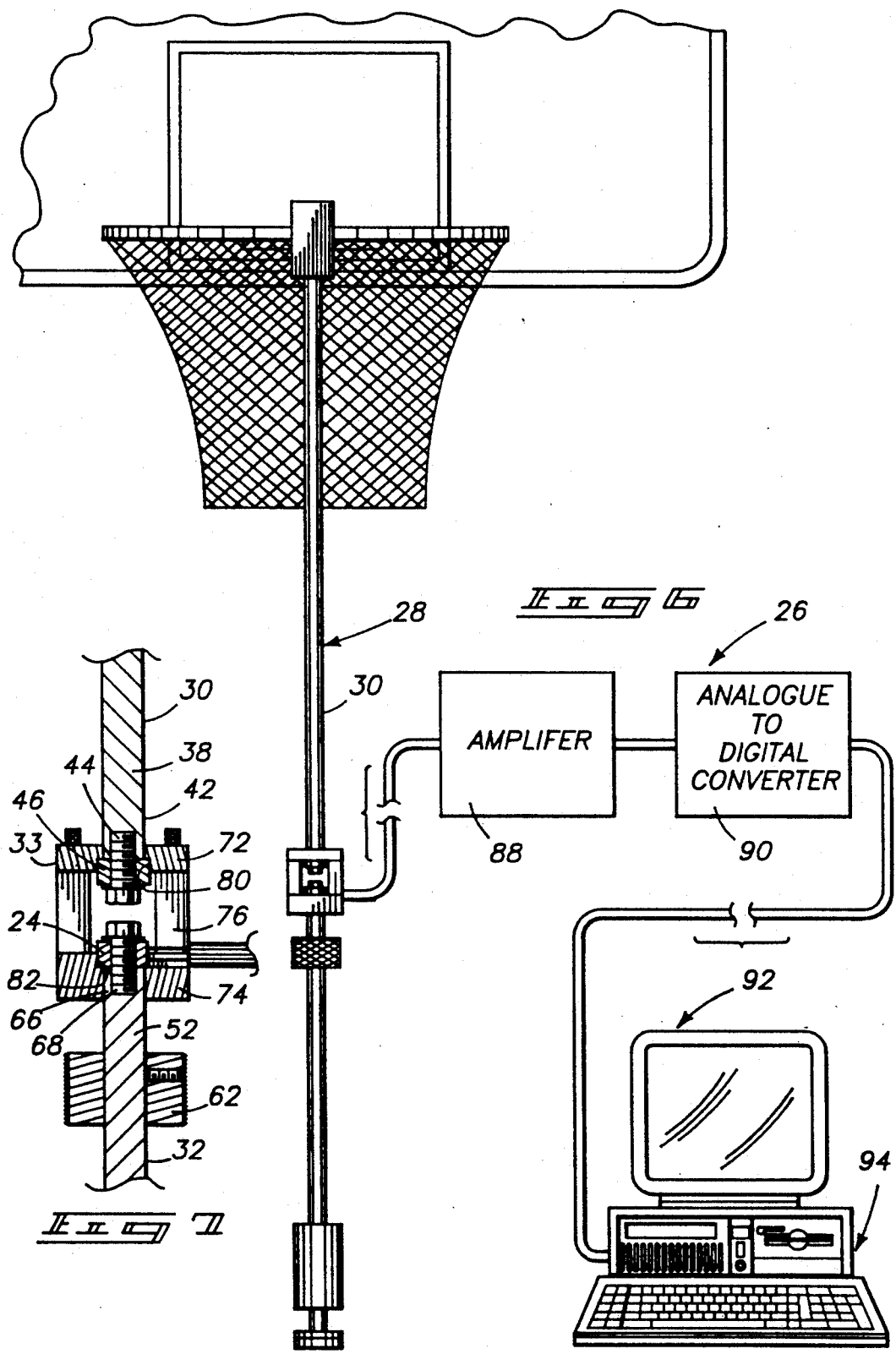

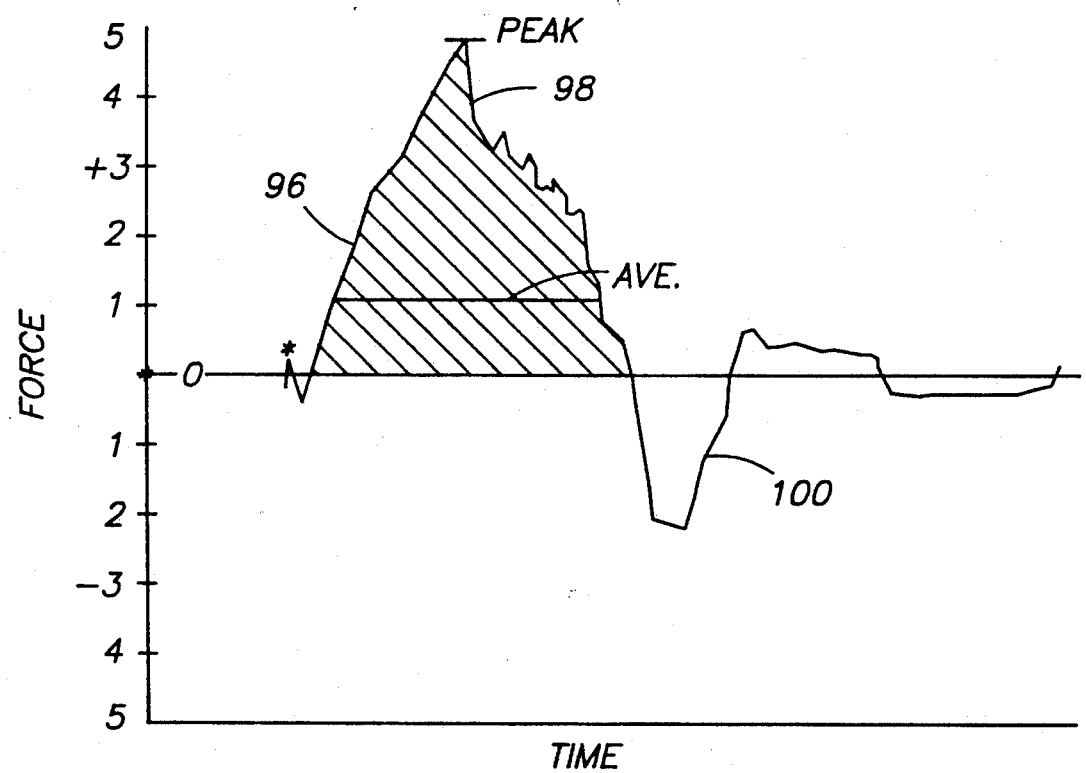

PORTABLE BASKETBALL RIM TESTING DEVICE

TECHNICAL FIELD

This invention relates to devices for determining the rebound characteristics of basketball rim systems.

BACKGROUND OF THE INVENTION

It has been found that the rebound characteristics of the basketball rim system can have a significant impact on the "play" of the game of basketball. For example, if a basketball rim system is a "lively" system, then it is more likely that the basketball will rebound a substantial distance from the basketball rim whereas a "dead" basketball rim will cause the basketball to rebound a shorter distance from the rim. Such different rebound characteristics change the location of the players attempting to regain the basketball when the basketball rebounds off the basketball rim.

Furthermore, it has been observed that "dead" basketball rims tend to increase the percentage of the basketball shots that pass through the goal. It has been observed that basketball games played utilizing "dead" basketball rims are higher scoring basketball games than those with "lively" basketball rims.

Because of the lack of standardization in the manufacturing of the basketball rim system, including (1) the material of the basketball rim, (2) its stress characteristics, (3) its design, (4) its method of connection with the backboard; and (5) its support system (ceiling, wall or floor), there can be a substantial difference in the "play" of the game. For example, if a team practices on a basketball court having "lively" basketball rim systems, they become accustomed to a particular rebound pattern of the basketball. Should the same team then play a basketball court having "dead" basketball rim systems, they will find that the basketball rebounds a shorter distance from the basketball rim and they will be out of position to recapture the ball when it rebounds from the basketball rim. Consequently, it is quite desirable to standardize the rebound characteristics of the basketball rim system so that the rebound "play" of the basketball is more uniform and does not give an undue advantage to the home team who is more likely accustomed to the rebound characteristics of the basketball rim system on their home court.

Furthermore, the rebound characteristics may favor one team versus another depending upon the height of the players. Generally a "dead" basketball rim favors the team having taller players that are clustered more closely to the basketball rim to recapture the basketball when it rebounds from the rim. Whereas a "lively" basketball rim favors a team having shorter players more likely clustered a further distance from the basketball rim.

For these reasons, there has existed for a substantial period of time, the desirability of a basketball rim testing device for testing the rebound characteristics of the basketball rim system to (1) determine its rebound characteristics, and (2) to determine if it falls within a permitted standard so that it does not give an undue advantage to the home team.

Although there has been a number of devices for testing the rebound characteristics of basketball rims, they have been difficult to administer, difficult to obtain standard comparisons between rims and difficult to obtain accurate and consistent information that will be acceptable to the coaching staffs of both teams and to the officials who officiate the game.

The principle object and advantage of this invention is to overcome these particular problems and to provide a portable basketball rim testing device for testing the rebound characteristics of the basketball rim system in a very efficient and reliable manner.

BRIEF DESCRIPTION OF THE DRAWINGS

The preferred embodiment of the invention is illustrated in the accompanying drawings, in which:

FIG. 1 is isometric view of a preferred embodiment of the basketball rim testing device illustrating the device mounted to a basketball rim;

FIG. 2 is a fragmentary isometric view of the portable basketball rim testing device;

FIG. 3 is an enlarged isolated view of a clamping means for securing the device to the basketball rim;

FIG. 4 is an exploded isometric view of a section of the device illustrating the mounting of a transducer;

FIG. 5 is an enlarged isometric view of a lower section of the device;

FIG. 6 is a front view of the device mounted on a basketball rim showing an electrical signal processing system in block diagram that is connected to a transducer;

FIG. 7 is a vertical cross-sectional view taken along line 7—7 in FIG. 2 illustrating the mounting of the transducer; and FIG. 8 is a graphic schematic view.

DETAILED DESCRIPTION OF THE PREFERRED EMBODIMENTS

The following disclosure of the invention is submitted in furtherance with the constitutional purpose of the Patent Laws "to promote the progress of science and useful arts" (Article 1, Section 8).

Referring to the drawings, there is illustrated in FIG. 1 a preferred embodiment of a basketball rim rebounding testing apparatus generally designated with the numeral 10 for determining the rebound or an elasticity characteristics of a basketball rim system 12. When referring to the basketball rim 12, one is generally referring to the entire basketball rim systems that supports the basketball rim in a cantilevered horizontal position. The rebound characteristics vary with the type and rigidity of the support system. For example, the basketball rim and backboard may be supported from a ceiling, from a wall or from a floor standing support structure. Frequently the basketball rim system 12 is portable so that it can be moved about on the basketball floor so that the basketball floor or gymnasium can be utilized for other events besides basketball. Consequently when it is stated that the apparatus 10 is intended to determine the elasticity or rebound characteristics of the basketball rim, such test is not limited to the basketball rim itself but is referring to the basketball rim system and how the system reacts to the basketball that impinges upon the rim. The basketball rim 12 is connected to a backboard 14 which is then supported by some type of support system from the ceiling, a wall, or the floor system. The basketball rim 12 is connected to the backboard 14 through a basketball rim bracket 16. The basketball rim 12 includes a net 18 that depends downward and generally somewhat inward from the rim.

The basketball rim 12 has an outer rim section 20 which is cantilevered from the backboard 14.

The basketball rim rebound testing apparatus 10 includes a force application means 22 for applying a downward vertical force on the outer rim section 20 to cause the outer rim section to deflect initially downward in response to the impact force. The apparatus or device 10 further includes a transducer 24 that measures the acceleration or force applied to the basketball rim and generates an electrical signal that contains information concerning the deflection, acceleration, and force application that are related to the elasticity of the basketball rim system. The apparatus or device 10 further includes a signal processing means 26 (FIG. 6) for receiving the electrical signal generated by the transducer 24 and in analyzing such information to determine the rebound characteristics. In the preferred embodiment illustrated, the device analyzes and determines the impulse that is exerted on the basketball rim which is characteristic of the elasticity of the basketball rim system 12 and consequently the rebound characteristics of the basketball rim system 12.

The force application means 22 includes a portable depending frame generally designated with the numeral 28 that is releasably connected to the basketball rim 12. The depending frame 28 includes an upper section 30, a lower section 32 and an intermediate transducer housing 33.

The upper section 30 includes a releasable attaching means for releasably attaching the apparatus 10 to the basketball rim. The attaching means preferably includes a "C" shaped hook 36 having a "C" shaped opening 37 for receiving the edge of the basketball rim 12. The upper section 30 has a rod 38 that extends downwardly therefrom in which the upper end of the rod 38 has a threaded section 40 (FIG. 2) that screws upward into the opening 37 to firmly clamp the basketball rim 12 in the opening 37. The rod 38 has a lower internally threaded end 42 (FIGS. 4 and 7) that threadably receives a bolt 44 that has an enlarged collar 46.

The lower section 32 includes a guide rod 52 having a lower end with a face plate 56. A ceramic washer 58 is mounted on the guide rod 52 bearing against the face plate 56 to receive the impact from a free cylindrical weight 60. The free cylindrical weight 60 has a low friction internal surface for sliding on the guide rod 52 to provide essentially a friction free fall for the weight 60 to impact against the ceramic washer 58 and the face plate 56 to bring the weight to a rapid and complete stop.

In a preferred embodiment, the cylindrical weight 60 has a weight of approximately 1.7 kilograms. The guide rod 52 has a length exceeding one meter. The lower end 32 includes adjustable stop 62 that is infinitely adjustable along the rod to set the stroke of the free weight 60. In one preferred embodiment, the adjustable stop 62 is fixed at approximately the one meter mark to permit the weight to drop one meter. The applicant has found that the 1.7 kilograms weight dropping one meter simulates a basketball being shot from approximately 20 feet from the basketball rim and impacting that outer rim section 20. The adjustable stop has a set screw for affixing the stop 62 at the desired elevation. In this manner, the weight can be set and have a constant stroke throughout the entire testing process to obtain uniformity of results. During some tests, it may be desirable to increase or decrease the stroke of the free weight to simulate basketballs that are shot from shorter distances or further distances from the basketball rim.

The guide rod 52 has an upper internally threaded end 66 that receives a bolt 68.

The transducer housing 33 (FIG. 4) includes an upper plate 72 and a lower plate 74 with four spaced legs 76 between the upper plate and the lower plate providing an internal cavity for receiving the transducer 24. Housing bolts 78 interconnect the upper plate and the lower plate to the legs 76. The upper plate 72 includes a recessed annular seat 80 that is complementary and receives the collar 46 as illustrated in FIGS. 4 and 7. Likewise a recessed seat 82 is formed in the lower plate 76 to receive the transducer 24. The transducer 24 is in the form of a piezoelectric ring 84 (FIG. 4) that fits within the recessed seat 82 and is essentially clamped between the bolt 68 and the lower plate 82 as illustrated in FIG. 7. When the weight 60 impacts the face plate 56 and ceramic washer 68, a sharp force is transmitted through the depending frame 68 to the basketball rim 12. Such force is measured by the compression of the piezoelectric ring 84 between the washer 70 and the lower plate 74 as illustrated in FIG. 7. The piezoelectric transducer 24 then transmits an electrical signal through transducer cable leads 86 to the signal processing means 26.

The signal processing means 26 (FIG. 6) includes an amplifier 88 for amplifying the signal generated by the piezoelectric transducer 24 to generate an analog signal representative of the magnitude of the force being applied to the basketball rim as measured by the piezoelectric transducer 24. The signal processing means 26 further includes an analog to digital converter 90 for converting the analog signal to digital signals representative of the magnitude of the force which additionally represents the magnitude of the deflection and the rate of the deflection. The signal generating means 26 additionally includes a sample and hold device 92 shown in the form of a personal computer that is programmed to sample the digital signals at defined intervals to obtained desired information from the A/D convertor 90.

As previously mentioned, the transducer 24 could be an accelerometer in which the information being transmitted is the acceleration of the basketball rim in the initial downward direction and then in the reverse upward direction as the basketball rim moves in a vibrational oscillating manner.

In addition, the signal processing means 26 includes a data analyzing means 94 which in this embodiment also includes the personal computer as illustrated in FIG. 6. The personal computer operates not only as a data acquisition system but also as a data analysis system. The information that is received from the sample and hold procedure is stored in memory for retrieval and analysis.

FIG. 8 illustrates a graph of the results of the tests showing a force curve 96 with respect to time. Curve 96 has a curved section 98 showing a positive force being exerted against the basketball rim as the basketball rim is deflected downwardly and then upwardly before the depending frame 28 becomes unweighted generating a negative force on the piezoelectric transducer. Upon initial calibration, of the device, the transducer is placed on a preload so that the unweighting of the system will produce a negative force which is illustrated by the curved section 100.

In the specific embodiment, the sample and hold device 92 samples the digital signal four thousand times per second. It is found that sufficient data is obtained by obtaining the first two hundred samples which is a measurement of approximately 50 milliseconds of time from the initial impact.

The data analysis system 94 is capable of then analyzing and determining the maximum force exerted on the basketball rim, the average force exerted on the rim during the sampling period (50 milliseconds). Probably most importantly is that the force is integrated over time (50 milliseconds) to determine the impulse or energy absorbed by the basketball rim 12.

In a preferred embodiment, the analysis of the data is conducted utilizing the commercially available software program called "Hyperplot" TM which is capable of analyzing the data and preparing the results that depict the rebound characteristics of the basketball rim system. In this embodiment, the sample and hold circuit 92 includes the personal computer when programmed utilizing a software program called "Quick Basic" TM sold by Microsoft, Inc. The applicant has found that the ring transducer 84 purchased from Kistler Piezo Instrumentation Corporation of Amhurst, N.Y. is preferred. The "Hyperplot" TM software is supplied by JMS Software Company.

As can be appreciated, the above described embodiment provides a very portable and reliable means of determining the rebound characteristics of a basketball rim system. The system can be easily moved from one rim to another so the entire test of two rims of a basketball court can be conducted in a period of less than an hour. Such tests can be conducted repetitively having accurate results that can be easily compared to determine rebound characteristics and determine if the rebound characteristics falls within any set standard. Additionally such a unit can be manufactured and sold for a reasonable amount to fit within the operating budget of most sports facilities.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

I claim:

1. A portable basketball rim testing device for determining the rebound characteristics of a basketball rim, comprising:
   frame adapted for connection to a basketball rim;
   force application means on the frame for applying a downward force of short duration having a magnitude sufficient to deflect the basketball rim to simulate the impact of falling basketball striking the basketball rim;
   transducer means on the frame and operatively connected to the basketball rim for generating a signal that is responsive to the deflection of the basketball rim caused by the application of the downward force; and
   signal processing means responsive to the transducer signal for determining the rebound characteristics of the basketball rim.

2. The portable basketball rim testing device of claim 1, wherein the transducer signal relates to the magnitude of the downward force applied to the basketball rim.

3. The portable basketball rim testing device of claim 1, wherein the transducer signal relates to the acceleration of the deflection of the basketball rim in response to the application of the downward force.

4. The portable basketball rim testing device of claim 1 wherein the transducer signal relates to the magnitude of deflection of the basketball rim.

5. The portable basketball rim testing device of claim 1 wherein the transducer signal relates to the elasticity characteristics of the basketball rim.

6. The portable basketball rim testing device of claim 1 wherein the transducer signal relates to the magnitude of deflection of the basketball rim and wherein the signal processing means monitors the transducer signal to determine both the magnitude of the deflection and the rate of change of the magnitude of the deflection.

7. The portable basketball rim testing device of claim 1, wherein the downward force applied to the rim is of sufficient magnitude to cause the basketball rim to initially deflect downward and then to rebound upward and wherein the signal processing means processes the transducer signal during the downward deflection and upward rebound.

8. The portable basketball rim testing device of claim 7, wherein the signal processing means analyzes the transducer signal to determine the time lapse during both the downward deflection and the upward rebound.

9. The portable basketball rim testing device of claim 1 wherein the downward force applied to the basketball rim is of sufficient magnitude to cause the basketball rim to initially deflect downward and then to rebound upward and wherein the signal processing means analyzes the transducer signal to determine characteristics of the initial downward deflection and upward rebound.

10. The portable basketball rim testing device of claim 1 further comprising attachment means for releasably attaching the force application means to the basketball rim.

11. The portable basketball rim testing device of claim 1 wherein the force application means includes a free falling weight of a known magnitude that is permitted to free fall a known distance and impact against a stop that is operatively connected to the basketball rim to generate and transmit the downward force to short duration to the basketball rim.

12. The portable basketball rim testing device of claim 1 wherein the transducer is a piezoelectric device for generating a signal responsive to the application of force to a piezoelectric crystal.

13. A portable basketball rim testing device for determining the rebound characteristics of a basketball rim, comprising:
   a weight guide;
   attachment means for attaching the weight guide to the basketball rim;
   a drop weight received by the weight guide;
   an impact face to terminate downward motion of the drop weight and to generate an impact force, the impact face being operably connected to the weight guide to transmit the impact force to the basketball rim, wherein the impact force has a magnitude sufficient to deflect the basketball rim to simulate the impact of a falling basketball striking the basketball rim;
   a transducer operably connected to the weight guide to generate a signal that contains information concerning the magnitude of the deflection of the basketball rim in response to the application of the impact force; and signal processing means responsive to the transducer signal for determining the rebound characteristics of the basketball rim.

14. The basketball rim testing device of claim 13, wherein the transducer signal contains information concerning the magnitude of the impact force applied to the basketball rim.

15. The basketball rim testing device of claim 13, wherein the transducer signal contains information concerning the acceleration of the basketball rim in response to the impact force.

16. The basketball rim testing device of claim 13, wherein the basketball rim has an initial downward deflection and a subsequent upward rebound, and wherein the signal processing means further analyzes the transducer signal during the downward deflection and upward rebound.

17. The basketball rim testing device of claim 13, wherein the signal processing means analyzes the transducer signal to determine an impulse measurement.

18. The basketball rim testing device of claim 13, wherein the signal processing means analyzes the transducer signal to determine a measurement of the peak force applied to the basketball rim.

19. The basketball rim testing device of claim 13, wherein the signal processing means analyzes the transducer signal to determine the response of the basketball rim to the impact force for a prescribed period of time.

20. The basketball rim testing device of claim 13, wherein the signal processing means additionally analyzes the transducer signal to determine a measurement of the average force applied to the basketball rim during a prescribed time period.

21. The basketball rim testing device of claim 13, wherein the signal processing means further analyzes the transducer signal to determine the time from initial impact to peak force application.

22. The basketball rim testing device of claim 13, wherein the drop weight has a mass of approximately 1.7 kilograms.

23. The basketball rim testing device of claim 13, further comprising an adjustable stop means on the weight guide for calibrating the impact force by adjusting the stroke of the drop weight.

24. The basketball rim testing device of claim 13, wherein the signal processing means further analyzes the transducer signal during a fixed measurement interval during transmission of the impact force.

25. The basketball rim testing device of claim 24, wherein the fixed measurement interval is approximately 0.05 seconds.

26. The basketball rim testing device of claim 24, wherein the signal processing means further comprises data processing means for repetitively measuring and storing the magnitude of the transducer signal for a fixed measurement interval during application of the impact force and for computing values representative of the basketball rim rebound characteristics from the stored magnitudes.

27. The basketball rim testing device of claim 24, wherein the data processing means has sampling means to store at least 200 magnitudes during the fixed measurement interval.

28. The basketball rim testing device of claim 24, wherein the fixed measurement interval is approximately 0.05 seconds.

29. The basketball rim testing device of claim 13, wherein the weight guide comprises a vertical rod for suspension from the basketball rim.

30. The basketball rim testing device of claim 13, wherein the attachment means included releasable gripping means for releasably gripping the basketball rim to transmit the impact force to the basketball rim and for enabling the device to be readily disconnected and removed from the basketball rim.

31. The basketball rim testing device of claim 29, wherein the vertical rod assembly has an upper section and a lower section and wherein:

the attachment means is on the upper section of the vertical rod assembly;

the drop weight is received by the lower section of the weight guide;

the impact face is located adjacent the lower end of the lower section;

the drop weight is slidably received by the lower section of the vertical rod; and the transducer is operably connected between the upper and lower sections of the vertical rod to measure the impact force transmitted to the basketball rim.

32. The basketball rim testing device of claim 31, further comprising a collar received by the lower section of the vertical rod for calibrating the impact force by limiting the stroke of the weight guide.

33. The basketball rim testing device of claim 31, further comprising a vertically adjustable collar slidably received by the lower section of the vertical rod for calibrating the impact force by limiting upward movement of the weight guide.

34. The basketball rim testing device of claim 31 wherein the transducer is mounted on the vertical rod assembly.

35. The basketball rim testing device of claim 32 wherein the transducer is a piezoelectric device for generating an electrical signal in response to the application of force to a piezoelectric crystal.

* * * * *